US008865660B2

(12) United States Patent
Broady

(10) Patent No.: US 8,865,660 B2
(45) Date of Patent: Oct. 21, 2014

(54) METHOD OF TREATING NEUROGENIC OVERACTIVE BLADDER IN A MAMMAL OR METHOD OF TREATING NON-PSYCHOLOGICAL STRESS-RELATED BLADDER DYSFUNCTION IN A FEMALE MAMMAL BY ADMINISTERING AT LEAST ON JASMONATE

(75) Inventor: Brunde Broady, New York, NY (US)

(73) Assignee: Broady Health Sciences, LLC, Coppell, TX (US)

( * ) Notice: Subject to any disclaimer, the term of this patent is extended or adjusted under 35 U.S.C. 154(b) by 0 days.

(21) Appl. No.: 13/316,443

(22) Filed: Dec. 9, 2011

(65) Prior Publication Data

US 2012/0149655 A1    Jun. 14, 2012

Related U.S. Application Data

(60) Provisional application No. 61/422,029, filed on Dec. 10, 2010.

(51) Int. Cl.
| | | |
|---|---|---|
| *A61K 31/19* | (2006.01) | |
| *A61K 31/122* | (2006.01) | |
| *A61K 31/215* | (2006.01) | |
| *A61K 31/365* | (2006.01) | |
| *A61K 31/7028* | (2006.01) | |

(52) U.S. Cl.
CPC ........... *B61K 31/122* (2013.01); *A61K 31/7028* (2013.01); *A61K 31/365* (2013.01); *A61K 31/215* (2013.01); *A61K 31/19* (2013.01)
USPC .......................................................... 514/25

(58) Field of Classification Search
None
See application file for complete search history.

(56) References Cited

U.S. PATENT DOCUMENTS

| | | | |
|---|---|---|---|
| 5,118,711 A | 6/1992 | Wilson | |
| 5,436,226 A | 7/1995 | Lulai | |
| 5,885,976 A | 3/1999 | Sandyk | |
| 6,100,287 A | 8/2000 | Stevens | |
| 6,143,784 A | 11/2000 | Greenhaff | |
| 6,191,156 B1 | 2/2001 | Kifor | |
| 6,265,421 B1 | 7/2001 | Pystynen | |
| 6,444,685 B1 | 9/2002 | Sum | |
| 6,465,021 B2 | 10/2002 | Bababunmi | |
| 6,469,061 B1 | 10/2002 | Flescher | |
| 6,514,991 B2 | 2/2003 | Coghlan | |
| 6,602,512 B1 | 8/2003 | Cavazza | |
| 6,887,499 B2 | 5/2005 | Bababunmi | |
| 7,279,479 B2 | 10/2007 | Levijoki | |
| 7,459,430 B2 | 12/2008 | Fraser | |
| 2002/0173470 A1 | 11/2002 | Flescher | |
| 2003/0021858 A1 | 1/2003 | Bababunmi | |
| 2003/0105104 A1* | 6/2003 | Burzynski | ..................... 514/251 |
| 2003/0187059 A1 | 10/2003 | Levin | |
| 2004/0266659 A1 | 12/2004 | LaBerge | |
| 2006/0111318 A1 | 5/2006 | Okamoto | |
| 2006/0165672 A1 | 7/2006 | Fuji | |
| 2006/0234939 A1 | 10/2006 | Fraser | |
| 2007/0042056 A1 | 2/2007 | Aoshima | |
| 2007/0142474 A1 | 6/2007 | Flescher | |
| 2008/0254055 A1 | 10/2008 | Oblong | |
| 2009/0018212 A1 | 1/2009 | Einstein et al. | |
| 2009/0291904 A1 | 11/2009 | Kashman | |
| 2009/0298936 A1 | 12/2009 | Clothier | |
| 2010/0003346 A1 | 1/2010 | Flescher | |
| 2010/0168040 A1 | 7/2010 | Komatsu | |
| 2011/0070181 A1 | 3/2011 | Williams | |
| 2011/0085999 A9 | 4/2011 | Dalko | |
| 2011/0287116 A1 | 11/2011 | Broady | |
| 2012/0172450 A1 | 7/2012 | Broady | |
| 2012/0288485 A1 | 11/2012 | Broady | |

FOREIGN PATENT DOCUMENTS

| | | | |
|---|---|---|---|
| JP | 2000355545 | 12/2000 | |
| WO | 0280890 | 3/2002 | |
| WO | 2005054172 | 6/2007 | |
| WO | 2009019693 | 2/2009 | |
| WO | WO 2010108012 A1 * | 9/2010 | ............. A01N 29/04 |

OTHER PUBLICATIONS

Ouslander, J.. Management of Overactive Bladder. New England Journal of Medicine, 350, 2004, pp. 786-799.*
Paul, A. B., Love, C., & Chisholm, G. D. (1994). The management of bilateral ureteric obstruction and renal failure in advanced prostate cancer. British journal of urology, 74(5), 642-645.*
Allen et al., "Impaired calcium release during fatigue", J. Appl. Physiol 104: 296-305. 2008.
Allo et al., "Non-insulin dependent diabetes-induced defect in cardiac cellular calcium regulation", Am. J. Physiol. 260: C1165-71. 1991.
Antipenko et al., "Comparison of the Effects of Phospholamban and Jasmone on the Calcium Pump of Cardiac Sarcoplasmic Reticulum", J. Biol. Chem. 272:2852-60 1997.
Assayag et al., "Senescent Heart Compared With Pressure Overload—Induced Hypertrophy", Hypertension 29:15-21. 1997.

(Continued)

*Primary Examiner* — Shaojia Anna Jiang
*Assistant Examiner* — Dale R Miller
(74) *Attorney, Agent, or Firm* — Cheryl H. Agris; Agris & Von Natzmer, LLP

(57) ABSTRACT

A formulation or composition contractility comprising jasmonate for modulating bladder and/or treating bladder dysfunction, particularly an overactive bladder in a mammal, particularly a human and use of jasmonate for treating bladder dysfunction is provided.

17 Claims, No Drawings

(56) References Cited

OTHER PUBLICATIONS

Chang et al., "Taurine protected myocardial mitochondria injury induced by hyperhomocysteinemia in rats", Amino Acids 27:37-48. 2004.
Ding et al. "Defective intracellular Ca2+ homeostasis contributes to myocyte dysfunction during ventricular remodelling induced by chronic volome overload in rats", Clin. Exp. Pharmacol. Physiol. 2008.
Fein et al., "Diabetic Cardiomyopathy", Cardiovasc Drugs Ther 8:65-73. 1994.
Frank, "Frequency dependent force generation correlates with sarcoplasmic calcium ATPase activity in human myocardium", Basic Res. Cardiol. 93: 405-411. 1998.
Frank, "Sarcoplasmic reticulum Ca -ATPase modulates cardiac contraction and relaxation", Cardiovasc. Res. 57: 20-27. 2003.
Heyliger et al.,"Effect of calmodulin on sarcoplasmic reticular Ca2+-transport in the aging heart", Mol. Cell Biochem. 1989.
International Search Report and Written Opinion for PCT/US11/36918, dated Jul. 19, 2012.
International Preliminary Report of Patentability for PCT/US11/36918, dated Nov. 20, 2012.
International Search Report and Written Opinion for PCT/US11/064286, dated Jul. 16, 2012.
International Search Report and Written Opinion for PCT/US12/37054, dated Aug. 23, 2012.
Joummaa et al., "Methyl Jasmonate-Induced Stimulation of Sarcoplasmic Reticulum Ca2+-ATPase Affects Contractile Responses in Rat Slow-Twitch Skeletal Muscle", J. Pharmacol. Exp. Ther. 300:638-46; 2002.
Kawase, et al., "Reversal of Cardiac Dysfunction After Long-Term Expression of SERCA2a by Gene Transfer in a Pre-Clinical Model of Heart Failure", J. Am. Coll. Cardiol. 51: 1112-1119. 2008.
Khan et al., "Istaroxime, a first in class new chemical entity exhibiting SERCA-2 activation and Na—K-ATPase inhibition: a new promising treatment for acute heart failure syndromes?", Heart Fail Rev. 14:277-87. 2009. (Epub Feb. 24, 2009).
Leppik et al., "Prolonged exercise to fatigue in humans impairs skeletal muscle Na+—K+-ATPase activity, sarcoplasmic reticulum Ca2+ release, and Ca2+ uptake" , J. Appl. Physiol. 97:1414-1423; 2004.
Leszek et al., "Alteration of myocardial sarcoplasmic reticulum Ca2+-ATPase and Na+—Ca2+ exchanger expression in human left ventricular volume overload", Eur. J. Heart Fail. 9:579-586. 2007.
Levin et al. "Biochemical evaluation of obstructive bladder dysfunction in men secondary to BPH: a preliminary report", Urology 53:446-450. 1999.
Li et al., "Effects of astragaloside IV on myocardial calcium transport and cardiac function in ischemic rats", Zi—Acta. Pharmacol. Sin. 23:898-904. 2002.
Li et al., "Effects of fatigue and training on sarcoplasmic reticulum Ca2+ regulation in human skeletal muscle", J. Appl. Physiol. 92:912-922; 2002.
Li et al., "The effect of 2-and 4-week ovariectomy on female rabbit urinary bladder function", Urology 74:691-697. 2009.
Maier et al, "Increased SR Ca2+ cycling contributes to improved contractile performance in SERCA 2a-overexpressing transgenic rats", Cardiovasc. Res. 67: 636-646. 2005.
Metra et al., "Vasodilators in the treatment of acute hear failure: what did we know, what we don't", Heart Fail Rev. 14: 299-307. 2009.
Nobe et al. "Phospholamban regulation of bladder contractility: evidence from gene-altered mouse models", J. Physiol. 535: 867-878. 2001.
Netticadan et al., "Depressed Levels of Ca2+-Cycling Proteins May Underlie Sarcoplasmic Reticulum Dysfunction in the Diabetic Heart", Diabetes. 50:2133-2138. 2001.
Ohara et al., "Effect of Diabetes on Cytosolic Free Ca2 + and Na+-K+—ATPase in Rat Aorta", Diabetes 40:1560-1563. 1991.

Ortenblad et al., "Impaired sarcoplasmic reticulum Ca2+ release rate after fatiguing stimulation in rat skeletal muscle", J. Appl. Physiol. 89:210-217. 2000.
Pieske et al., "Sarcoplasmic reticulum Ca2+ load in human heart failure", Basic Res. Cardiol. 97 suppl. 1: 163-171. 2002.
Prestle et al., "Ca2+-Handling Proteins and Heart Failure: Novel Molecular Targets?", Curr. Med. Chem. 10: 967-981. 2003.
Rocchetti et al., "Modulation of Sarcoplasmic Reticulum Function by PST2744 [Istaroxime; (E,Z)-3-(2-Aminoethoxy)imino) Androstane-6,17-dione Hydrochloride)] in a Pressure-Overload Heart Failure Model", J. Pharmacol. Exp. Ther. 326:957-965. 2008. (Epub Jun. 8, 2008).
Sakata et al., "Mechanical and Metabolic Rescue in a Type II Diabetes Model of Cardiomyopathy by Targeted Gene Transfer", Mol. Ther. 13:835-838. 2006.
Schmidt et al., "Contribution of Abnormal Sarcoplasmic Reticulum ATPase Activity to Systolic and Diastolic Dysfunction in Human Heart Failure", J. Mol. Cell Cardiol. 30: 1929-1937. 1998.
Schultz et al., "Accelerated onset of heart failure in mice during pressure overload with chronically decreased SERCA2 calcium pump activity", Am J Physiol Heart Circ Physiol. 286: H1146-H1153. 2004.
Starling et al., "Mechanism of stimulation of the calcium adenosinetriphosphatase by jasmone", Biochemistry 33:3023-31. 1994.
Starling et al, "Evidence that the effects of phospholipids on the activity of the Ca2+ ATPase do not involve aggregation", Biochem. J. 308:343-6. 1995.
Steele et al., "Metabolic factors contributing to altered Ca2+ regulation in skeletal muscle fatigue", Acta. Physiol. Scand. 179:39-48. 2003.
Tate et al., "Mechanisms for the responses of cardiac muscle to physical activity in old age", Med. Sci. Sports Exerc. 26:561-567. 1994.
Trost et al., "Overexpression of the Sarcoplasmic Reticulum Ca2+-ATPase Improves Myocardial Contractility in Diabetic Cardiomyopathy", Diabetes 51:1166-1171. 2002.
Tupling, "The sarcoplasmic reticulum in muscle fatigue and disease: role of the sarco (endo) plasmic reticulum Ca2+-ATPase", Can J Appl Physiol 29:308-329. 2004.
Vangheluwe, "New perspectives on the role of SERCA2's Ca2+ affinity in cardiac function", Biochim. Biophys. Acta 1763:1216-1228. 2006.
Vasanji et al., "Increased inhibition of SERCA2 by phospholamban in the type I diabetic heart", Mol. Cell Biochem. 261:245-249. 2004.
Williams et al., "Contractile apparatus and sarcoplasmic reticulum function: effects of fatigue, recovery, and elevated Ca2+", J. Appl. Physiol. 83:444-450. 1997.
Xu et al., "Modification of alterations in cardiac function and sarcoplasmic reticulum by astragaloside IV in myocardial injury in vivo", Eur. J. Pharmacol. 568:203-212. 2007. (Epub Apr. 19, 2007).
Yoshikawa et al., 2004, "Energy utility of failing heart", Nippon Yakurigaku Zasshi 123:77-86. 2004. (English abstract).
Zhang et al. , Antagonism for different doses of taurine on calcium overload in myocardial cells of diastole heart failure rat model, Zhongguo Zhong Yao Za Zhi 34:328-331. (English abstract).
Zhao et al. "Correlation of ischemia/reperfusion or partial outlet obstruction-induced spectrin proteolysis by calpain with contractile dysfunction in rabbit bladder", Urology 49: 293-300 1997.
Zhao et al., "Decreased cardiac sarcoplasmic reticulum Ca2+-ATPase activity contributes to cardiac dysfunction in streptozotocin-induced diabetic rats", J. Physiol. Biochem . 62:1-8. 2006.
Ziegelhoffer et al., "Diabetic cardiomyopathy in rats: biochemical mechanisms of increased tolerance to calcium overload", Diabetes Res. Clin. Pract. 31 Suppl:S93-103. 1996.
Acuna-Castroviejo et al., "Melatonin is Protective Against MPTP-Induced Striatal and Hippocampal Lesions", Life Sciences 60: 23-29. 1997.
Al-Aama et al., "Melatonin decreases delirium in elderly patients: A randomized, placebo-controlled trial", Int. J. Geriatric Psych. 26: 687-694 (epub 2010).

(56) References Cited

OTHER PUBLICATIONS

Anisimov et al., "Dose-dependent effect of melatonin on life span and spontaneous tumor incidence in female SHR mice", Exper. Gerontol. 38: 449-461.2003.
Chen et al., "Ca(2+)+Mg2+]-dependent ATPase activity in rat pineal gland", Neuroscience Lett. 157: 131-4. 1993.
Davies et al., "AKR1C Isoforms Represent a Novel Cellular Target for Jasmonates alongside Their Mitochondrial-Mediated Effects", Cancer Research. 69:4. 4769-4775. 2009.
International Search Report and Written Opinion for PCT/US2011/064288, dated Dec. 28, 2012.
Mattera et al., "Sympathomimetic inefficiency in restoring contractility in the acute or chronic b-blocker-treated ischaemic heart:Comparison with a new agent", Eur. J. Heart Fail. 10:990-996. 2008. (Epub Aug. 6, 2008).
Morton et al., "Involvement of calcium in pineal gland function", Proc Soc Exp Biol Med 197:378-83. 1991.
Pappolla et al., "Melatonin prevents death of neuroblastoma cells exposed to the Alzheimer amyloid peptide", Neurosci 17: 1683-90. 1997.
Reiter et al., "Attenuated nocturnal rise in pineal and serum melatonin in a genetically myopathic Syrian Hamster with a deficient calcium pump", J Pineal Res. 11: 156-62. 1991.
Reiter, "The pineal gland and melatonin in relation to aging: a summary of the theories and of the data", Exper. Gerontol. 30: 199-212. 1995.
Reiter, "Oxidative damage in the central nervous system: protection by melatonin", Prog Neurobiol. 56: 359-389. 1998.
Venkataraman et al. "Protective role of melatonin on PCB (Aroclor 1254) induced oxidative stress and changes in acetylcholine esterase and membrane bound ATPases in cerebellum, cerebral cortex and hippocampus of adult rat brain", Int. J. Dev Neurosci 26: 585-591. 2008.
Williams et al., "Functional aspects of skeletal muscle contractile apparatus and sarcoplasmic reticulum after fatigue", J. Appl. Physiol. 85:619-626. 1998.
Zhao et al., "Pineal perifusion with calcium channel blockers inhibits differently daytime and nighttime melatonin production in rat", Mol. Cell. Endocrinol. 101: 189-96. 1994.
Bendahan et al., "Citrulline/ malate promotes aerobic energy production in human exercising muscle" Br. J. Sports Med. 36:282-289. 2002.
Campbell et al., "Pharmacokinetics, safety, and effects on exercise performance of L-arginine α-ketoglutarate in trained adult men" Nutrition 22: 872-881. 2006.
Frank et al., "Modulation of SERCA: Implications for the failing human heart" Basic Res. Cardiol. 97: Suppl 1,1/72-1/78. 2002.
Miyazaki et al. "Optimal and effective oral dose of taurine to prolong exercise performance in rat", Amino Acids 27: 291-298. 2004.
Zoladz et al., "Cognitive enhancement through stimulation of of the chemical senses" North American J. Psychol. 7.1: 125-140. 2005.
Non-Final Office Action dated May 9, 2013 for U.S. Appl. No. 13/467,606.
Non-Final Office Action dated Jun. 19, 2013 U.S. Appl. No. 13/316,441.
Non-Final Office Action dated Oct. 7, 2013 for U.S. Appl. No. 13/110,146.
Foreign Office Action and Foreign Associate's analysis for Taiwan App. No. 100145466, counterpart to U.S. Appl. No. 13/316,441.
Foreign Office Action and Foreign Associate's analysis for Taiwan App. No. 100145467, counterpart to U.S. Appl. No. 13/316,443.
International Preliminary Report of Patentability for PCT/US11/64286, dated Jun. 20, 2013.
International Preliminary Report of Patentability for PCT/US11/64288, dated Jun. 12, 2013.
International Preliminary Report of Patentability for PCT/US12/37054, dated Nov. 21, 2013.

* cited by examiner

METHOD OF TREATING NEUROGENIC OVERACTIVE BLADDER IN A MAMMAL OR METHOD OF TREATING NON-PSYCHOLOGICAL STRESS-RELATED BLADDER DYSFUNCTION IN A FEMALE MAMMAL BY ADMINISTERING AT LEAST ON JASMONATE

TECHNICAL FIELD

A formulation or composition comprising jasmonate for treating bladder dysfunction, particularly an overactive bladder in a mammal, particularly a human and use of jasmonate for treating bladder dysfunction is provided.

BACKGROUND

Bladder Dysfunction

Bladder dysfunction is caused by abnormal functioning of the bladder tissue resulting in dysuria, irritative symptoms of urgency, frequency and nocturinia and the obstructive symptoms of reduced flow rate, incomplete emptying, hesitancy and increased time to urinate. One type of bladder dysfunction is an overactive bladder. This may be due to a number of factors.

One such cause of an overactive bladder is benign prostrate hyperplasia (BPH), a common condition in aging men. Approximately 80% of men over 50 years of age have varying degrees of urinary bladder outlet obstruction secondary to BPH (Levin et al., 1999, Urology 53:446-450). The bladder dysfunction symptoms are related to the effect of the enlarged prostrate on the urethra which creates a partial urethral obstruction.

The urethral obstruction caused by the enlarged prostrate initiates compensatory changes in the bladder including increased bladder wall thickness, decreased compliance, and detrusor denervation which are mediated by three cellular processes: 1) reduced nerve density; 2) mitochondrial dysfunction and 3) dysregulation of calcium storage and release from the sarcoplasmic reticulum involving $Ca^{2+}ATPase$ dysfunction (see, for example, US 2003/0187059).

$Ca^{2+}ATPase$ activities are approximately 40% lower in bladder samples of men with benign prostate hyperplasia (BPH) mediated bladder dysfunction as compared to $Ca^{2+}$ ATPase levels of bladder samples obtained from men of similar ages with no obstructive symptoms (Levin et al., 1999, Urology 53:446-450). The contractile dysfunctions associated with partial outlet obstruction correlate with disrupted sarcoplasmic reticulum (SR) $Ca^{2+}$ storage release mechanisms and the degree of the contractile dysfunction is directly proportional to the degradation of sarcoplasmic endoplasmic reticulum calcium ATPase (SERCA) as shown using both enzymatic activity assays and Western blot analysis (see, for example, Zhao et al., 1997, Urology 49: 293-300).

Bladder dysfunction, particularly overactive bladder and more particularly, incontinence and poor detrusor contraction in women all increase as a function of age (reviewed in Li et al., 2009, Urology 74:691-697). A study presented by the Bladder Health Council of the American Foundation for Urologic Disease stated that incontinence affects more than 10 million Americans 85% who are women and affects over 20% of women over the age of 45 and the number increases with age.

In women, alterations in the female sex hormones are believed to play a major role in mediating symptoms of an overactive bladder such as including incontinence, urgency, and frequency due to observed weakness of urethral and pelvic floor muscles and underactive detrusuor smooth muscle contraction in low estrogen states. A possible explanation for the dysfunction is that there is a direct relationship between estrogen levels and blood flow to the bladder and urethral tissue which increases free radical generation and oxidative damage. The oxidative damage associated with estrogen levels as a result of reduced blood flow to the bladder and urethra could account for the decreased $Ca^{2+}ATPase$ activity associated with the bladder and the urethra in low estrogen states such as menopause. Total $Ca^{2+}ATPase$ activity of both the muscle and mucosa was significantly reduced in ovarectomized rabbits (OX) after 28 days indicating that calcium storage and release are compromised after OX (Li et al., 2009, Urology 74:691-697).

Other causes of outlet obstruction that results in bladder dysfunction include but are not limited to cancer, sclerosis or fibrosis of the bladder neck, urethral structure disease, urethral valves, and smooth and striated sphincter dyssynergia, (reviewed in US 2006/0234939). Furthermore, children may suffer from congenital urethral obstruction (U.S. Pat. No. 6,191,156).

An overactive bladder may also occur as a result of neurological damage due to disorders including but not limited to stroke, Parkinson's disease, diabetes, multiple sclerosis, peripheral neuropathy or spinal cord lesions.

Various therapies have been tried to treat bladder dyfunction, particularly overactive bladders. These include but are not limited to anticholinergic agents, prostaglandin inhibitors, beta-adrenergic agonists, COX2 inhibitors, calcium channel modulators (see, for example, U.S. Pat. Nos. 6,444, 685, 6,19,156, 6,514,991, 7,459,430). Additionally, it has been observed that phospholamban, an inhibitor of SERCA is present in bladder sarcoplasmic reticulum and may play a role in bladder contractility (Nobe et al., 2001, J. Physiol. 535: 867-878).

Jasmonates

Jasmonates are a family of plant stress hormones that are found in minute quantities in edible plants and characterized by cyclopentone rings. Various uses for jasmonates have been disclosed. Examples include enhancing plant growth (U.S. Pat. No. 5,436,226), repelling insects (U.S. Pat. No. 5,118, 711), treating cancer (U.S. Pat. No. 6,469,061) and treating skeletal muscle degeneration caused by malnutrition and disease (U.S. Pat. No. 6,465,021, US Patent Appln. Pub. No. 201000003346), pain relief (WO 2009019693), relieving psychological stress (US Patent Appln. Pub. No. 200700420567), use as a component of a sleep supplement (JP2000355545), treating dry skin (US Patent Appln. Pub. No. 20110085999), treating malodors on fabrics (US Patent Appln. Pub. No. 20110070181) treating heart failure and related disorders (US2011. Jasmonate has also been found to increase $Ca^{2+}Atpase$ in cardiac sarcoplasmic reticulum (see, for example, Antipenko et al., 1997, J. Biol. Chem. 272:2852-60) and skeletal muscle (see, for example, Ioumaa et al., 2002, J. Pharmacol. Exp. Ther. 300:638-46; Starling et al, 1995, Biochem. J. 308:343-6 and Starling et al., 1994, Biochemistry 15:3023-31).

SUMMARY

Provided is a method for modulating bladder contractility in a subject in need thereof comprising administering an amount of at least one jasmonate and optionally at least one other substance, wherein said substance is a drug or natural substance used to treat bladder dysfunction, effective to modulate said bladder contractility. In a related aspect, the invention relates to a method for treating bladder dysfunction, particularly, non-psychological stress related bladder dysfunction, even more particularly, an overactive bladder in a subject comprising administering an amount of at least one jasmonate effective to treat said bladder dysfunction, particularly, non-psychological stress related bladder dysfunction, even more particularly, an overactive bladder which even more particularly is an age-related overactive bladder and/or non-psychological stress related overactive bladder. In a particular embodiment, the subject is a mammal and in an even more particular embodiment, the subject is human.

Further provided, are compositions for modulating bladder contractility and/or non-psychological stress related bladder dysfunction in a mammal (e.g., human) comprising at least one jasmonate and optionally at least one other substance, wherein said substance may be a drug or natural substance used to treat said bladder dysfunction. The substance may be an antioxidant, a vitamin, amino acid and/or nutritional supplement. The composition may comprise jasmonate (e.g., methyl jasmonate), at least two basic amino acids (e.g., arginine and citrulline) and a nutritional supplement (e.g. taurine). The composition may comprise jasmonate, arginine, citrulline and taurine. In particular, the composition may comprise methyl jasmonate, arginine, citrulline and taurine or alternatively, cis-jasmone, arginine, citrulline and taurine.

In a related aspect, also provided is the use of jasmonate and optionally one other substance, wherein said substance is a drug or natural substance used to treat bladder dysfunction, particular an overactive bladder (e.g., age related overactive bladder), for formulating a medicament for use in modulating bladder contractility and/or for treating bladder dysfunction (e.g., non-psychological stress related bladder dysfunction), particularly an overactive bladder (e.g., age related overactive bladder, non-psychological stress related overactive bladder) in a mammal (e.g., human).

DETAILED DESCRIPTION OF SPECIFIC EMBODIMENTS

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

It must be noted that as used herein and in the appended claims, the terms "composition" and "formulation" are used interchangeably.

DEFINITIONS

As defined herein, the term "modulate" means adjusting amount and/or rate of bladder contractility. Preferably, bladder contraction is stimulated.

As defined herein, the term an "overactive bladder" is any type of lower urinary tract disorder characterized by increased frequency of a desire to void, whether complete or episodic and where lost of voluntary control ranges form partial to total and where there is loss of urine (incontinence) or not. Symptoms include, but are not limited to, urinary urgency, incontinence, urge incontinence, urinary frequency and nocturia.

Jasmonates

The jasmonates used in the compositions and methods disclosed herein may have the formula I

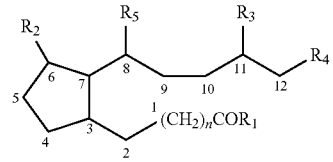

Formula I wherein:
n is 0, 1, or 2;
$R_1$ is OH, alkoxy, O-glucosyl, or imino,
$R_2$ is OH, O, alkoxy, or O-glucosyl,
$R_3$, $R_4$, and $R_5$ are H, OH, alkoxy or O-glucosyl,
and/or wherein $R_1$ and $R_2$, or $R_1$ and $R_4$ together form a lactone, and further wherein the bonds between $C_3$:$C_7$, $C_4$:$C_5$, and $C_9$:$C_{10}$ may be double or single bonds; or a derivative of said formula, wherein the derivative has at least one of the following:
a lower acyl side chain at $C_3$ (free acid or ester or conjugate), a keto or hydroxy (free hydroxy or ester) moiety at the $C_6$ carbon, or an n-pentenyl or n-pentyl side chain at $C_7$.

In a particular embodiment, the jasmonate may be at least one member selected from the group consisting of methyl jasmonate, jasmonic acid, jasmone, 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 4,5-didehydro-7-iso-jasmonic acid, cucurbic acid, 6-epi-cucurbic acid, 6-epi-cucurbic-acid lactone, 12-hydroxy-jasmonic acid, 12-hydroxy-jasmonic-acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside 5,6-didehydrojasmonic acid, 6,7-didehydro-jasmonic acid, 7,8-didehydrojasmonic acid, cis-jasmone, methyl-dihydro-isojasmonate, dihydro-jasmone, amino acid conjugates of jasmonic acid, the lower alkyl esters of said jasmonic acids, and the carrier ligand conjugates and the sterioisomers thereof.

Compositions

The compositions may comprise the jasmonate set forth above. Additionally, the compositions may further comprise least one other drug or natural substance used to modulate bladder contractility and/or treat bladder dysfunction, particularly non-stress related bladder dysfunction, even more particularly, an overactive bladder, even yet more particularly, age-related overactive bladder. This drug or substance may include but is not limited to substances that will be effective in treating bladder dysfunction and particularly an overactive bladder and/or that potentiates the effect of jasmonate. Such substances may include but are not limited to duloxetine, monoamine reuptake inhibitors, spasmolytics, anticholinergics, beta-3 adrenergic receptor agonists (see, for U.S. Pat. Nos. 6,444,685 and 6,569,873), calcium sensitizers, antioxidants (see, for example, US 2003/0187059), calcium channel modulators (see, for example, US 2006/0234939).

The compositions may also include jasmonates in combination with a drug or substance that may include but is not limited to Astragalus or substances derived therefrom (e.g., astragaloside), gingerol, taurine, green tea or substances derived therefrom (e.g., epigallocatechin gallate), gingerol, amino acids such as taurine and arginine and citrulline. In a particular embodiment, the composition may comprise methyl jasmonate, arginine, citrulline and taurine.

The compositions, in particular, pharmaceutical compositions can be formulated for administration by a variety of routes including oral, transdermal, parenteral (subcutaneous, intraperitoneal, intravenous, intra-arterial, and intramuscular). The compositions may also be formulated for transurethral administration and may be in the form of in the form of a suppository (see, for example, US 2006/0234939). Alternatively, the compositions may be formulated for vaginal administration and may be in the form of vaginal suppositories, creams, ointments, liquid formulations, pessaries, tampons, gels, pastes, foams or sprays (See, for example, US 2006/0234939).

Such compositions are prepared in a manner well known in the pharmaceutical art and comprise as an active ingredient at least one of the compounds used in the methods as described herein above and a pharmaceutically acceptable excipients or a carrier. The amount of the active ingredient(s) in the composition of the present invention is from about 0.5 to 100% per weight. The term "pharmaceutically acceptable" means approved by a regulatory agency of the Federal or a state government or listed in the U.S. Pharmacopeia or other generally recognized pharmacopeia for use in animals and, more particularly, in humans. Choosing suitable ingredients for the composition is a routine for those of ordinary skill in the art. It is evident that suitable carriers, solvents, gel forming ingredients, dispersion forming ingredients, antioxidants, colors, sweeteners, wetting compounds, release controlling components and other ingredients normally used in this field of technology may be also used. Pharmaceutical compositions in the form of intravenous solutions are preferred. The active ingredients may be formulated in the same pharmaceutical formulation. Alternatively, the active ingredients are formulated as separate pharmaceutical dosage forms. The combination of the pharmaceutical dosage forms may be packaged as a single medical product or kit for use in the method of the invention, optionally together with a package insert instructing to the correct use of the medical product.

Another preferred embodiment of the invention is a medical product comprising, separately or together, as active ingredients one or more jasmonates or a pharmaceutically acceptable salt thereof and one or more other substance used for reducing muscle fatigue and/or increasing skeletal muscle performance in a mammal as a combined preparation.

In yet another embodiment, the medical product may comprise one two or more jasmonates set forth above in separate compositions.

Administration and Uses

As noted above, one or more jasmonate(s) optionally in combination with other substances may be used to treat bladder dysfunction, particularly, non-stress related bladder dysfunction. In a specific embodiment, the jasmonate optionally in combination with other substances may be used to treat an overactive bladder, in particular a non-stress related overactive bladder. Non-psychological stress related overactive bladder includes but is not limited to age-related overactive bladder or neurogenic overactive bladder. An age-related overactive bladder may in particular embodiment, be due to prostate hyperplasia, a disorder associated with benign enlargement of the prostate gland or in another embodiment an estrogen deficiency associated with menopause. A neurogenic overactive bladder may in one embodiment occur as a result of neurological damage due to disorders including but not limited to stroke, Parkinson's disease, diabetes, multiple sclerosis, peripheral neuropathy or spinal cord lesions.

The active ingredients may be administered simultaneously, separately or sequentially. The administration routes of the active ingredients include, but are not limited to, enteral, e.g. oral or rectal, or parenteral, e.g. intravenous, intramuscular, transurethral, vaginal, intraperitoneal or transdermal.

The active ingredients furthermore may be administered as an immediate release formulation (a drug formulation that provides for release of the drug immediately after drug administration) controlled release formulation (a formulation in which release is not immediate) or a sustained release formulation (a drug formulation that provides for gradual release of a drug over an extended period of time, and that preferably, although not necessarily, results in substantially constant blood levels of a drug over an extended time period such as up to about 72 hours, about 66 hours, about 60 hours, about 54 hours, about 48 hours, about 42 hours, about 36 hours, about 30 hours, about 24 hours, about 18 hours, about 12 hours, about 10 hours, about 8 hours, about 4 hours, after drug administration). In a particular embodiment, the compositions may be administered prior to commencement of an activity where suppression of symptoms of an overactive bladder would be desirable.

The compositions used may preferably be administered orally preferably once per day. According to the invention, the suggested daily dose of jasmonate(s) is in general from about 0.01 to 50 mg, preferably from about 0.02 to 20 mg, more preferably from about 0.05 to 10 mg, and even more preferably, from about 0.05 mg-0.10 mg, depending on the age, body weight and condition of the patient. The effective amount of jasmonate(s) to be administered to a subject depends upon the condition to be treated, the route of administration, age, weight and the condition of the patient. Similar dosages of other substances may also be used.

EXAMPLES

The composition and methods set forth above will be further illustrated in the following, non-limiting Examples. The examples are illustrative of various embodiments only and do not limit the claimed invention regarding the materials, conditions, weight ratios, process parameters and the like recited herein.

Five subjects, 4 male and 1 female agreed to participate in the study. Subjects ranged in age from 55-73 with average age being 67. All participants experienced noticeable urinary bladder dysfunction symptoms including frequency, urgency, and reduced urine flow. Subjects took from 50 to 100 micrograms of Jasmone once a day for 30 days. At two weeks approximately ½ of the subjects experienced improved bladder function. By day thirty, all subjects reported improvements in frequency, urgency, and urine flow. For example, several subjects noted that before treatment they averaged 2 night time awakenings to urinate which was reduced to 1 or 0 subsequent to taking Jasmone. Other subjects had even greater improvement from an average of 3-4 night awakenings to urinate to 1. Daytime bathroom visits were also reduced approximately 50%. Several patients also noted radically reduced urgency, which increased "holding time" from approximately 10 minutes to 60 minutes i.e. during extended air travel. In addition several male subjects reported increased flow of discharge up to 100%.

This invention may be embodied in other forms or carried out in other ways without departing from the spirit or essential characteristics thereof. The present disclosure is therefore to be considered as in all aspects illustrate and not restrictive, and all changes which come within the meaning and range of equivalency are intended to be embraced therein.

Various references are cited throughout this specification, each of which is incorporated herein by reference in its entirety.

What is claimed is:

1. A method for treating a neurogenic overactive bladder in a mammal in need thereof comprising administering an amount of at least one jasmonate effective to treat said neurogenic overactive bladder.

2. The method according to claim 1, wherein said jasmonate has the structure (I)

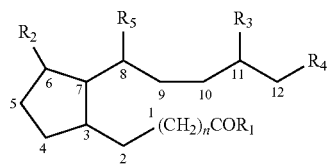

wherein:
n is 0, 1, or 2;
$R_1$ is OH, alkoxy, O-glucosyl, or imino,
$R_2$ is OH, O, alkoxy, or O-glucosyl,
$R_3$, $R_4$, and $R_5$ are H, OH, alkoxy or O-glucosyl,
and/or wherein $R_1$ and $R_2$, or $R_1$ and $R_4$ together form a lactone, and further wherein the bonds between $C_3:C_7$, $C_4:C_5$, and $C_9:C_{10}$ may be double or single bonds; or a derivative of said structure, wherein said derivative is a jasmonate of structure I modified by one or more substituents selected from the group consisting of a lower acyl free acid, ester or conjugate side chain at $C_3$, a keto, hydroxy and ester moiety at the $C_6$ carbon, or an n-pentenyl or n-pentyl side chain at $C_7$.

3. The method according to claim 2, wherein said jasmonate is a compound selected from the group consisting of methyl jasmonate, jasmonic acid, jasmone, 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 4,5-didehydro-7-iso-jasmonic acid, cucurbic acid, 6-epi-cucurbic acid, 6-epi-cucurbic-acid lactone, 12-hydroxy-jasmonic acid, 12-hydroxy-jasmonic-acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, 5,6-didehydrojasmonic acid, 6,7-didehydro-jasmonic acid, 7,8-didehydrojasmonic acid, cis-jasmone, methyl-dihydro-isojasmonate, dihydro-jasmone, amino acid conjugates of jasmonic acid, the lower alkyl esters of said jasmonic acids, and the stereoisomers thereof.

4. The method according to claim 1, which further comprises administering at least one other substance, wherein said substance is a drug or natural substance, wherein said drug or natural substance is used to treat an overactive bladder.

5. The method to claim 4, wherein said substance is a drug or natural substance, wherein said drug or natural substance is an antioxidant, a vitamin, amino acid, nutritional supplement, or combination of the foregoing.

6. The method according to claim 4, wherein jasmonate, citrulline, arginine and taurine are administered to said mammal.

7. A method for modulating bladder contractility and/or treating non-psychological stress-related bladder dysfunction in a female mammal in need thereof comprising administering an amount of at least one jasmonate effective to modulate said bladder contractility and/or to treat said non-psychological stress related bladder dysfunction.

8. The method according to claim 7, wherein said non-psychological stress related bladder dysfunction is an age-related overactive bladder.

9. The method according to claim 8, wherein said age-related overactive bladder is due to estrogen deficiency associated with menopause.

10. The method according to claim 7, wherein said female mammal is a human woman.

11. The method according to claim 7, wherein said jasmonate has the structure (I)

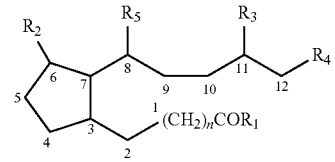

wherein:
n is 0, 1, or 2;
$R_1$ is OH, alkoxy, O-glucosyl, or imino,
$R_2$ is OH, O, alkoxy, or O-glucosyl,
$R_3$, $R_4$, and $R_5$ are H, OH, alkoxy or O-glucosyl,
and/or wherein $R_1$ and $R_2$, or $R_1$ and $R_4$ together form a lactone, and further wherein the bonds between $C_3:C_7$, $C_4:C_5$, and $C_9:C_{10}$ may be double or single bonds; or a derivative of said structure, wherein said derivative is a jasmonate of stricture I modified by one or more substituents selected from the group consisting of a lower acyl free acid, ester or conjugate side chain at $C_3$, a keto, hydroxy or ester moiety at the $C_6$ carbon, or an n-pentenyl or n-pentyl side chain at $C_7$.

12. The method according to claim 7, wherein said jasmonate is a compound selected from the group consisting of methyl jasmonate, jasmonic acid, jasmone, 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 4,5-didehydro-7-iso-jasmonic acid, cucurbic acid, 6-epi-cucurbic acid, 6-epi-cucurbic-acid lactone, 12-hydroxy-jasmonic acid, 12-hydroxy-jasmonic-acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, 5,6-didehydrojasmonic acid, 6,7-didehydro-jasmonic acid, 7,8-didehydrojasmonic acid, cis-jasmone, methyl-dihydro-isojasmonate, dihydro-jasmone, amino acid conjugates of jasmonic acid, the lower alkyl esters of said jasmonic acids, and the stereoisomers thereof.

13. The method according to claim 7, which further comprises administering at least one other substance, wherein said substance is a drug or natural substance, wherein said drug or natural substance is used to modulate bladder contractility and/or treat bladder dysfunction.

14. The method to claim 13, wherein said substance is a drug or natural substance, wherein said drug or natural substance is an antioxidant, a vitamin, amino acid, nutritional supplement, or combination of the foregoing.

15. The method according to claim 13, wherein jasmonate, citrulline, arginine and taurine are administered to said mammal.

16. The method according to claim 1, wherein said jamonate is selected from the group consisting of tuberonic acid-O-β-glucopyranoside and cucurbic acid-O-β-glucopyranoside.

17. The method according to claim 7, wherein said jamonate is selected from the group consisting of tuberonic acid-O-β-glucopyranoside and cucurbic acid-O-β-glucopyranoside.

* * * * *